(12) United States Patent
Haran et al.

(10) Patent No.: US 8,314,391 B2
(45) Date of Patent: Nov. 20, 2012

(54) CONTROLLING THE BENDS IN A FIBER OPTIC CABLE TO ELIMINATE MEASUREMENT ERROR IN A SCANNING TERAHERTZ SENSOR

(75) Inventors: Frank Martin Haran, North Vancouver (CA); Ross MacHattie, Mississauga (CA); Ron E Beselt, Burnaby (CA); David Jez, Vancouver (CA)

(73) Assignee: Honeywell ASCa Inc., Mississauga (CA)

( * ) Notice: Subject to any disclaimer, the term of this patent is extended or adjusted under 35 U.S.C. 154(b) by 933 days.

(21) Appl. No.: 12/008,244

(22) Filed: Jan. 9, 2008

(65) Prior Publication Data

US 2010/0282970 A1 Nov. 11, 2010

Related U.S. Application Data

(60) Provisional application No. 61/009,647, filed on Dec. 31, 2007.

(51) Int. Cl.
*G01N 21/01* (2006.01)
(52) U.S. Cl. .................................................. 250/341.1
(58) Field of Classification Search ................ 250/341.1
See application file for complete search history.

(56) References Cited

U.S. PATENT DOCUMENTS

| | | |
|---|---|---|
| 4,767,935 A | 8/1988 | Anderson et al. |
| 4,786,817 A | 11/1988 | Boissevain et al. |
| 4,830,503 A | 5/1989 | Hoda et al. |
| 4,920,261 A | 4/1990 | Bock et al. |
| 4,982,334 A | 1/1991 | Balakrishnan |
| 5,022,966 A | 6/1991 | Hu |
| 5,396,055 A | 3/1995 | Shepard et al. |
| 5,539,634 A | 7/1996 | He |
| 5,773,714 A | 6/1998 | Shead |
| 5,952,818 A | 9/1999 | Zhang et al. |
| 6,665,075 B2 | 12/2003 | Mittleman et al. |
| 6,747,736 B2 | 6/2004 | Takahashi |
| 7,214,940 B2 * | 5/2007 | Cluff et al. .................. 250/341.1 |
| 7,242,010 B2 | 7/2007 | Liu et al. |
| 2002/0074500 A1 | 6/2002 | Mickan et al. |
| 2006/0109519 A1 | 5/2006 | Beselt et al. |
| 2006/0243931 A1 | 11/2006 | Haran et al. |
| 2007/0158571 A1 * | 7/2007 | Cole et al. .................. 250/341.8 |

OTHER PUBLICATIONS

L.P. Schmidt et al., THz Measurements Technologies and Applications, Microwaves, Radar & Wireless Communications, 2002, MIKON-2002, vol. 2, pp. 581-587.

Peter H. Siegel, Terahertz Technology, IEEE Transactions on Microwave Theory and Techniques, vol. 50, No. 3, Mar. 2002, p. 910-928.

* cited by examiner

*Primary Examiner* — Constantine Hannaher
(74) *Attorney, Agent, or Firm* — Cascio Schmoyer & Zervas

(57) ABSTRACT

A terahertz time-domain spectrometer scanning sensor system includes a transmitter and a receiver that are secured to a mobile scanner head. Optical pump light, in the form of short pulses launched from a stationary laser located remotely from the scanner head, is delivered to the transmitter and receiver through a controlled fiber optic cable arrangement so that variations in temporal pulse relays that are associated fiber optic transmission are minimized. In this fashion, the movement of the fiber optic cable is maneuvered along a defined path so as to control the bends in the cable and thus minimize variations in temporal delays that can otherwise arise as the pulses of light are transmitted through the fiber. Pulses of laser light launched from the laser into the optical fiber will exit the cable with consistent (i) time of arrival, (ii) phase duration, and (iii) polarization state and energy.

10 Claims, 3 Drawing Sheets

CONTROLLING THE BENDS IN A FIBER OPTIC CABLE TO ELIMINATE MEASUREMENT ERROR IN A SCANNING TERAHERTZ SENSOR

REFERENCE TO RELATED APPLICATIONS

This application claims priority to U.S. Provisional Application 61/009,647 that was filed on Dec. 31, 2007.

FIELD OF THE INVENTION

The present invention generally relates to scanning sensors that employ terahertz radiation for detecting the presence of specific components in paper and other sheet products. In particular, the technique employs a terahertz time-domain spectrometer whereby optical pump light, in the form of short pulses from a laser, is delivered to the transmitter and receiver through a controlled fiber optic cable arrangement so that variations in temporal pulse delays that would otherwise arise as the pulses of light are transmitted through the fiber optic cable are minimized or eliminated.

BACKGROUND OF THE INVENTION

It is often desirable to obtain measurements of selected characteristics of sheet materials during manufacture. Although various properties of sheet materials can be detected by off-line laboratory testing, this procedure is often not practical because of the time required for sample acquisition and analysis. Also, laboratory testing has the shortcoming that samples obtained for testing may not accurately represent sheet material that has been produced.

To overcome the drawbacks of laboratory testing of sheet materials, various sensor systems have been developed for detecting sheet properties "on-line," i.e., on a sheet-making machine while it is operating. Typically, on-line sensor devices are operated to periodically traverse, or "scan," traveling webs of sheet material during manufacture. Scanning usually is done in the cross direction, i.e., in the direction perpendicular to the direction of sheet travel. Depending upon the sheet-making operation, cross-directional distances can range up to about twelve meters or more.

Terahertz systems known as terahertz time-domain spectrometers (THz-TDS) often use laser pulses each lasting only 10 to 200 femtoseconds to generate, detect, and measure electromagnetic pulses ("T-rays") that each last for about a picosecond. T-rays can be transmitted through various objects, using an imaging system of lenses and mirrors to focus or collimate the T-rays. As the T-rays pass through the object under test, they are typically distorted. These changes in the T-ray signals can be analyzed to determine properties of the object. Materials can be characterized by measuring the amounts of distortion-from absorption, dispersion and reflection-of the T-rays passing through to a detector. A digital signal processing unit processes the data and translates it into data that appear on a computer screen. The digital signal processor takes the digitized data from the THz detector and analyzes the data in either the spectral or temporal domain.

Because many compounds change T-rays in characteristic ways (e.g., absorption or dispersion), molecules and chemical compounds, show strong absorption lines that can serve as "fingerprints" of the molecules. T-ray spectroscopy can distinguish between different chemical compositions inside a material even when the object looks uniform in visible light. Typical THz-TDS devices are designed for batch applications and therefore are not suitable for deployment for on-line applications.

SUMMARY OF THE INVENTION

The present invention is based in part on the recognition that in order to use THz-TDS for sensing applications in real-time industrial processes where scanning is employed, a fiber optic cable is employed to deliver the optical pump light over relatively long distances to the THz transmitter and receiver of the sensor. The optical pump light is preferably delivered in the form of short pulses which are typically 10 to 200 femtoseconds (fs) in duration. Similarly, signals from the receiver are transmitted to a spectrometric analyzer through a fiber optic cable. A feature of the invention is that a take-up mechanism is employed to control the movement of the fiber optic cables so as to minimize variations in temporal delays due to transmission through the fiber and thereby substantially reduce or eliminate measuring errors of the sensor. Pulses of light transmitted through the moving fiber optic cable will exhibit consistent (i) time of arrival, (ii) phase duration, and (iii) polarization state and energy Accordingly, one aspect of the invention is directed to a scanning sensor system, for moving a scanning terahertz sensor head, which measures at least one selected property in a sample, between a first end and a second end along a main scanning direction, which includes:

a laser source that generates pulses of radiation;

means for splitting the pulses of radiation to yield first radiation pulses and second radiation pulses;

a transmitter that generates terahertz frequency signal pulses when excited by the first radiation pulses from the laser source, wherein the transmitter is configured to direct the terahertz frequency signal pulses to the sample and wherein the transmitter is secured to a mobile carriage;

a first optical fiber having a first end and a second end, wherein the first radiation pulses are directed into the first end such that pulses of radiation that are transmitted through the first optical fiber exit at the second end and are directed to the transmitter;

a detector for receiving terahertz frequency radiation that emerges from the sample and that generates detection signals when excited by the second radiation pulses;

a second optical fiber having a first end and a second end, wherein the second radiation pulses are directed into the first end such that pulses of radiation that are transmitted through the second optical fiber exit at the second end and are directed to the detector, wherein the first optical fiber and the second optical fiber move through a take-up mechanism as the mobile carriage moves along the main scanning direction; and means for driving a mobile carriage along the main scanning direction.

In a preferred embodiment, both the first and second optical fibers are encased in the same cable structure so that both fibers are subject to the same degree of bending as they are maneuvered through the take-up mechanism and both are exposed to the same temperature gradients. In this fashion, both the source pump light (first radiation pulses) and the detector gating light (second radiation pulses) travel essentially identical path lengths and the differential delay between these two light paths is minimized.

In another aspect, the invention is directed to an on-line scanning sensor system capable of detecting one or more characteristics of a traveling sheet of product such as paper as it progresses through or exits from a sheet-making machine that includes:

a support member spanning across the traveling sheet of product;

a mobile carriage, that is slidably attached to the support member, onto which a transmitter is secured, wherein the transmitter generates terahertz frequency signal pulses when excited by pulses of radiation and wherein the transmitter is configured to direct the terahertz frequency signal pulses to the traveling sheet;

a laser source that generates pulses of radiation and that is located remotely from the mobile carriage;

means for splitting the pulses of radiation to yield first radiation pulses and second radiation pulses;

a first optical fiber having a first end and a second end, wherein the first radiation pulses are directed into the first end such that pulses of radiation that are transmitted through the first optical fiber exit at the second end and are directed to the transmitter;

a detector for receiving terahertz frequency radiation that emerges from the sample and that generates detection signals when activated by the second radiation pulses;

a second optical fiber having a first end and a second end, wherein the second radiation pulses are directed into the first end such that pulses of radiation that are transmitted through the second optical fiber exit at the second end and are directed to the detector, wherein the first optical fiber and the second optical fiber move through a take-up mechanism as the mobile carriage moves along the main scanning direction; and means for driving a mobile carriage between a first end and a second end along a main scanning direction such that the mobile carriage scans back and forth across at least a substantial portion of the product along a cross direction of the moving sheet.

In a further aspect, the invention is directed to a method of performing measurements, with a scanning terahertz sensor that detects at least one selected property in a sample between a first end and a second end along a main scanning direction, that includes the steps of:

(a) securing a transmitter to a mobile carriage wherein the transmitter generates terahertz frequency signal pulses when excited by pulses of radiation and wherein the transmitter is configured to direct the terahertz frequency signal pulses to the traveling sheet;

(b) providing a laser source that laser generates pulses of radiation and that is located remotely from the mobile carriage;

(c) splitting the pulses of radiation to yield first radiation pulses and second radiation pulses;

(c) providing a first optical fiber having a first end and a second end, wherein the first radiation pulses are directed into the first end such that pulses of radiation that are transmitted through the first optical fiber exit at the second end and are directed to the transmitter;

(d) providing a detector for receiving terahertz frequency radiation that emerges from the sample and that generates detection signals;

(e) providing a second optical fiber having a first end and a second end, wherein the second radiation pulses are directed into the first end such that pulses of radiation that are transmitted through the second optical fiber exit at the second end and are directed to the detector;

(f) moving the mobile carriage between a first end and a second end along a main scanning direction; and (g) operating the laser source to launch pulses of radiation into the first optical fiber and second optical fiber.

DESCRIPTION OF PREFERRED EMBODIMENTS

Figure 1:
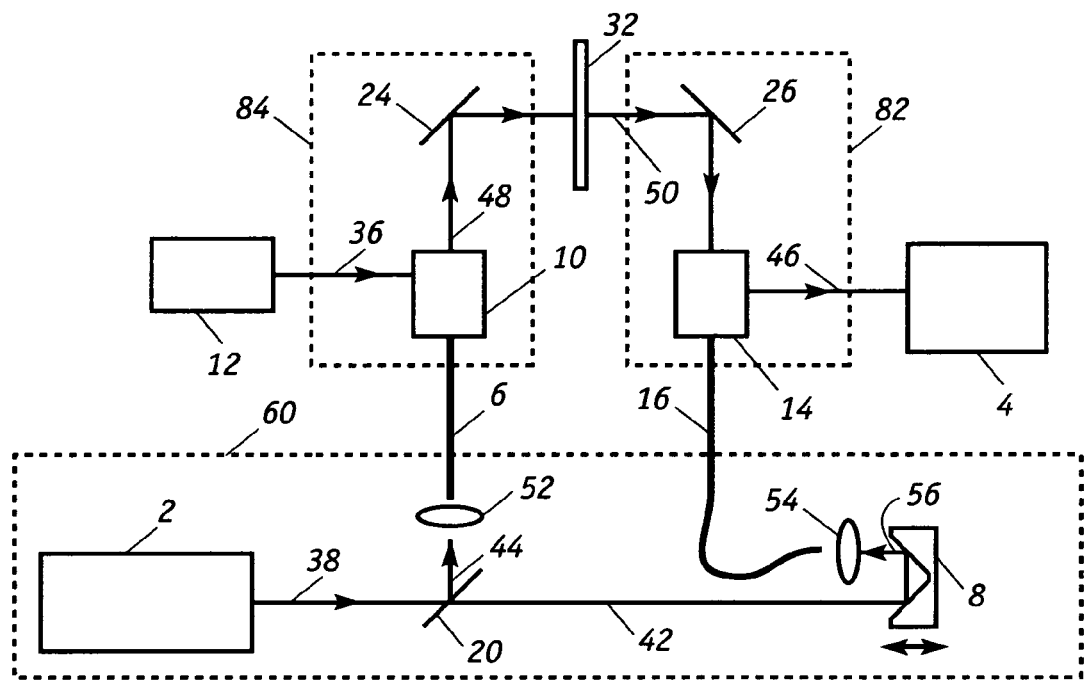
FIG. 1 illustrates a scanning terahertz sensor system.

FIG. 1 shows the structure of a terahertz time-domain spectrometer for monitoring at least one property of the moving sheet or web of material 32. The basic components of the spectrometer include: pulsed laser source 2, beam splitter 20, terahertz transmitter 10, modulated power source 12, terahertz receiver or detector 14, spectroscopic analyzer 4, and optical delay device 8, each of which consists of a conventional device. Pulsed laser source 2, such as a femto-second pulse laser, generates pump signals 38 that are directed toward beam splitter 20 which splits the light pulses of pump signal 38 to yield excitation light 44 and detector gating light 42.

Excitation light 44 is focused by objective lens 52 and launched into and transmitted through delivery fiber optic cable or optical fiber 6. Excitation light 44 illuminates transmitter 10 to generate terahertz radiation or T-rays 48 which are directed by mirror 24 into moving sheet 32. Modulated power source 12 supplies an electrical input 36 into terahertz transmitter 10. T-rays 50 which emerge from the moving sheet 32 are reflected from mirror 26 and captured by detector 14. Mirrors 24 and 26 when employed are typically off-axes parabolic mirrors.

Figure 2A:
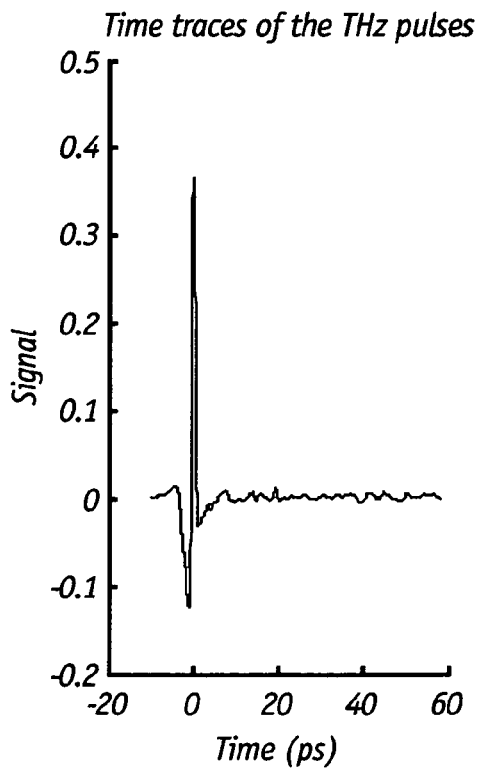
FIG. 2A shows a temporal THz pulse from a THz transmitter and FIG. 2B shows the Fourier transform of the time trace.
Figure 2B:
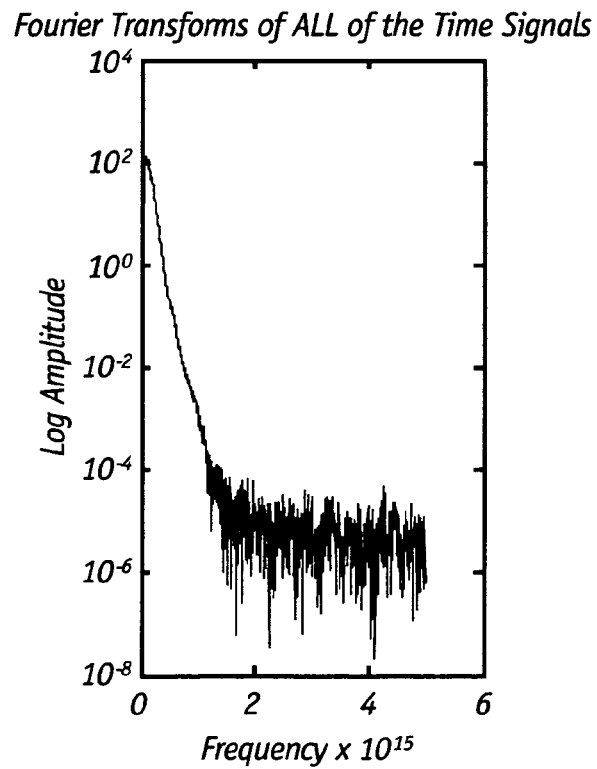

Detector gating light 42 is directed to optical delay device 8 which serves to set or modify the difference between the timing of the detector gate light 42 and the timing of the excitation light 44. Optical delay device 8 includes a movable retro-reflector. Changing the position of movable retro-reflector changes the length of the optical path of detector gating light 42, thereby changing and setting the difference between excitation light irradiation timing (T-ray generating timing) and the detector gating light irradiation timing (T-ray detecting timing). Objective lens 54 directs detector gating light 56 from optical delay device 8 and launches the light into delivery fiber optic cable or optical fiber 16 and into receiver or detector 14. The laser pulses that exit from the end of fiber optical cable 16 are used to effectively switch on the terahertz receiver in a synchronous detection scheme. When the arrival time of these synchronizing pulses to the terahertz receiver are varied, the terahertz pulses can be traced out as illustrated in FIG. 2A. FIG. 2B shows the processed Fourier transform of the time trace. The output 46 from receiver 14 is an electrical signal that is typically amplified and digitized and then read into a computer for analysis or alternatively the electrical signal can be analyzed in a digital signal processor. The electrical signal can be amplified with a transimpedance amplifier and then fed into a lockin amplifier. If lockin detection is employed, a modulated bias voltage is typically applied to power source 12. The lockin detector is then synchronized with this bias modulation.

Detector 14 generates detection signals 46 which are transmitted to spectroscopic analyzer 4, which is typically a computer. The electrical signals generated by the detector that can be analyzed in the computer in the temporal or frequency domain. For instance, this analysis can also be done in a Field-Programmable Gate Array (FPGA) or a Digital Signal Processor (DSP).

While optical delay device 8 is positioned in the optical path of detector light 42, an optical delay device could be positioned in the optical path of excitation light 44 instead. Preferably, laser source 2, beam splitter 20, optical delay device 8, and objective lens 52 and 54 are housed in compartment 60. In a transmission mode embodiment, terahertz transmitter 10 and mirror 24 are located in sensor head 84 whereas detector 14 and mirror 26 are located in sensor head 82. The sensor head can be any suitable light weight structure housing the associated components.

If optical rectification is used to generate or detect the THz radiation, then optical fibers are preferably selected from those which can maintain the linear polarization state of the light which is injected into them since the THz transmitter and receiver are dependent upon the polarization state of the pump light. Preferred optical fibers are highly birefringent or single polarization photonic bandgap fiber which will maintain the polarization of the femto-second pulse laser generated pulses of light. It is often preferable to use a THz antenna to both generate and receive the THz radiation, in which case, using non-polarization maintaining optical fibers are preferred since the generation and detection of the THz radiation is not polarization sensitive.

In order to function as a scanning terahertz sensor, sensor heads 82 and 84 must be mobile which means that movement of fiber optic cables 6 and 16, which are in optical communication with sensor heads 84 and 82, respectively, must also be accommodated. As further described herein, fiber optic cables 6 and 16 are routed through take-up mechanisms to control the bending of the cables.

Figure 3A:
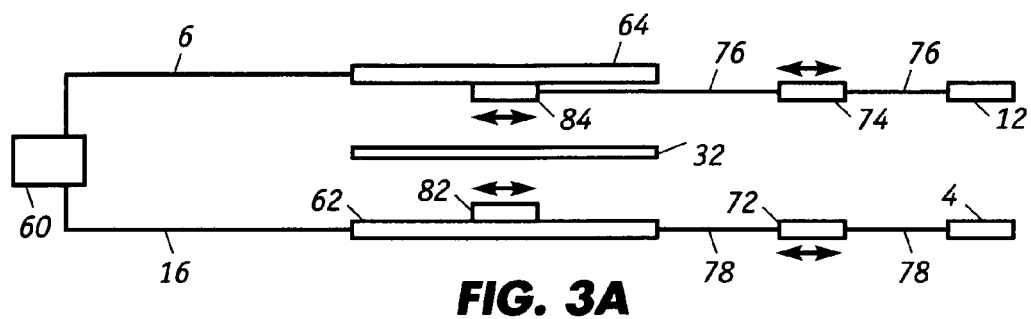
FIG. 3A illustrates the scanning terahertz sensor in the transmission geometry.

FIG. 3A depicts the take-mechanism in relationship to the components of the scanning terahertz sensor for the transmission geometry where sensor head 84 is designed to travel back and forth along the cross-direction along the main scanning direction of moving sheet 32 such as paper in a papermaking machine. This width can be one to twelve meters or more. The terahertz transmitter within compartment 60 is in optical communication with fiber optic cable 6 which is routed through take-up mechanism 64. Suitable up-take mechanisms are described in U.S. patent application Ser. No. 2006/0109519 to Beselt et al., which is incorporated herein by reference. As sensor head 84 moves from one edge of sheet 32 to the other, the take-up mechanism controls the bends in the fiber optic cable. Modulated power source 12 is in electrical communication with terahertz transmitter 10 via line or wire 76 which can be incorporated into a conventional mobile power chain or track 74. Similarly, for sensor head 82, which is also designed to move along the cross-direction of moving sheet 32, the detector within sensor head 82 is in optical communication with fiber optic cable 16, which is routed through take-up mechanism 62. Finally, analyzer 4 is in electrical communication via line or wire 78 with the detector within sensor head 82. Wire 78 can be incorporated into a conventional mobile power chain or track 72.

In operation, the movements of the dual scanner heads 82, 84 are synchronized with respect to speed and direction so that they are aligned with each other. Scanning systems having sensor components on opposite sides of the sheet being analyzed are described, for example, in U.S. Pat. No. 5,773,714 to Shead and U.S. Pat. No. 5,166,748 to Dahlquist, which are incorporated herein by reference. Preferably, compartment 60, modulated power source 12 and analyzer 4 are all located in stationary positions remote from scanner heads 82 and 84 for easy access for repairs and away from the harsh environment of the sheet making machine.

Figure 3B:
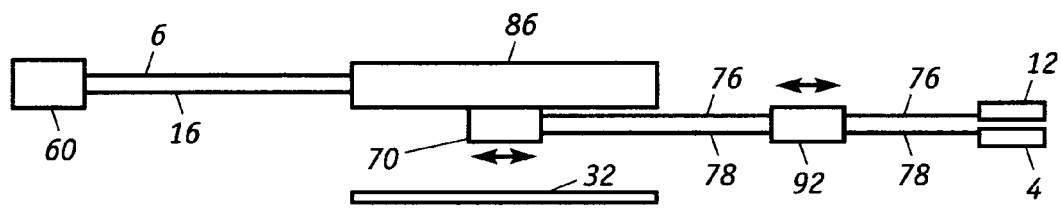
FIGS. 3B and 3C illustrate the scanning terahertz sensor in the reflection geometry.
Figure 3C:
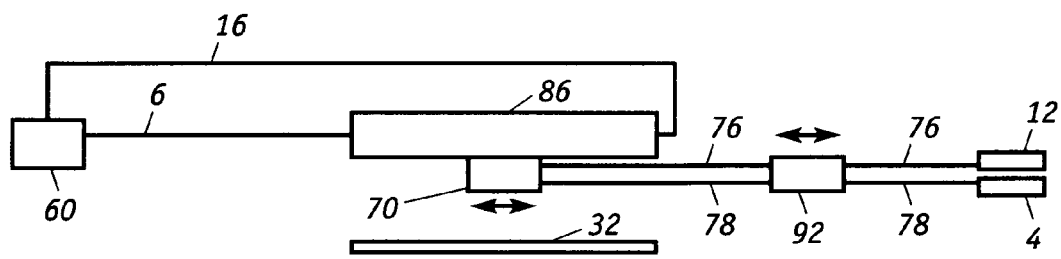

FIGS. 3B and 3C depict the take-mechanism in relationship to the components of the scanning terahertz sensor for the reflection geometry. In the embodiment of FIG. 3B, terahertz transmitter 10, detector 14 and mirrors 24 and 26 (FIG. 1) are housed in sensor head 70. Fiber optic cables 6 and 16 can be bundled together in a single cable and routed through take-up mechanism 86 and thus provide optical communication between components within compartment 60 and components within sensor head 70. Wires 76 and 78 which can be incorporated into a mobile power track provide 92 electrical communication between modulated power source 12 and analyzer 4 and components within sensor head 70. Compartment 60, modulated power source 12 and analyzer 4 are preferably all located in stationary positions remote from scanner head 70.

An advantage to having delivery fiber optic cables 6 and 16 in the same cable structure is that both cables experience the same temperature environment which may be important where there are temperature variations in the scanning sensor system. Alternatively, instead of having the two cables in one structure, the two cables can be deployed side-by-side, in which case, the pulleys of the take-up mechanism will have double grooves as further described herein.

Finally, FIG. 3C depicts an alternative embodiment wherein scanning terahertz sensor having a single sensor head 70 is configured for operating in the reflection mode. Terahertz transmitter 10, detector 14 and mirrors 24 and 26 (FIG. 1) are housed in sensor head 70 but fiber optic cables 6 and 16 are routed separately through the same take-up mechanism 86 as described further herein. This arrangement is particularly suitable where the fiber optic cables are not exposed to significant temperature variations. Optical communication between components within compartment 60 which contains and components within sensor head 70 is maintained. Wires 76 and 78 which can be incorporated into a mobile power track 72 provide electrical communication between modulated power source 12 and analyzer 4 and components within sensor head 70.

Figure 4A:
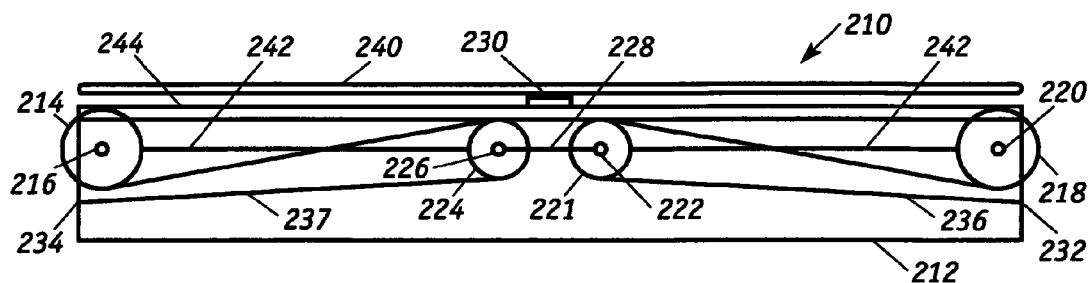
FIGS. 4A and 4B are side schematic views of a fiber optic cable take-up mechanism.
Figure 4B:
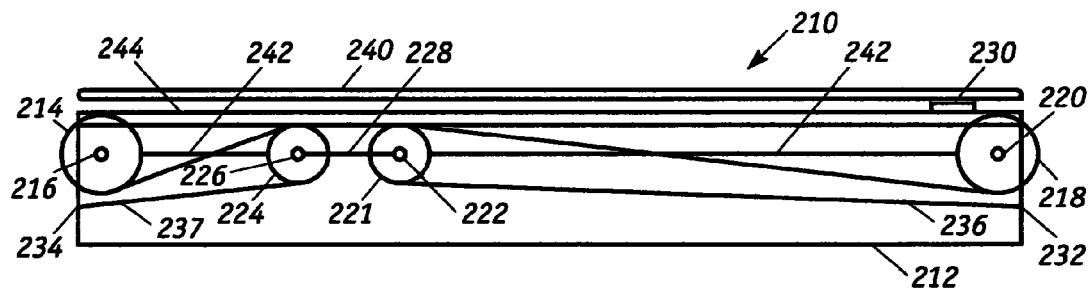

FIGS. 4A and 4B illustrate an embodiment of a cable take-up mechanism 210 that facilitates the movement of scanner head 230 along the cross direction of a moving sheet or web 240. The take-up mechanism will minimize variations in temporal delays attendant to transmission through the fiber optic cable. The result is that pulses of light transmitted through the moving fiber will exhibit consistency in at least one (or all of) the following characteristics: (i) relative arrival times of transmitter and receiver pump pulses, (ii) phase duration of pump pulses, (iii) polarization state, and (iv) energy of pump pulses.

Located on one side of frame 212 is a first fixed turning pulley 214 which is secured to the frame by pin 216. Positioned on the other side of the frame is second fixed turning pulley 218 which is secured by pin 220. The distance between pins 216 and 220 preferably ranges from one to twelve meters. The diameters of the two fixed turning pulleys 214, 218 are preferably the same. Each pulley preferably has a groove around its outer perimeter that is dimensioned to accommodate a flexible cable.

Situated within frame 212 and positioned between the two fixed pulleys 214, 218 are a pair of movable or translating pulleys 221, 224 that are linked to each other by a rigid member 228. The pair of movable pulleys 221, 224 is secured by pins 222 and 226, respectively, to a rail 242 which allows the movable pulleys 221, 224 to move back-and-forth along a linear path between the fixed turning pulleys 214, 218. Preferably, the diameters of the movable pulleys 221 and 224 are the same but they are preferably smaller than the diameters of the fixed turning pulleys 214, 218. The centers of the four pulleys 214, 218, 221 and 224 are preferably aligned along a horizontal axis.

In the case where the terahertz sensor is operating in the reflection mode so that only a single take-up mechanism is required as shown in FIG. 3C, a fiber optic cable 236, representing fiber optic cable 6 (FIG. 1), is partially wound around pulleys 221 and 218. Cable 236 terminates at sensor head 230 while the cable at position 232 is secured to frame 212 or other stationary structure. Another fiber optic cable 237, representing fiber optic cable 16 (FIG. 1), is partially wound around pulleys 224 and 214. Cable 237 also terminates at sensor head 230 while the cable at position 234 is secured to frame 212 or other stationary structure. Both cables 236 and 237 should be secured with sufficient tension to avoid excessive slack. No spring or other tension device is needed to secure the two ends.

The scanner head 230 is operatively connected to the cables 236 and 237 as it scans back and forth along the cross direction between the sides of the moving sheet 240. The linked translating pulleys 221, 224 move in the opposite direction to that of scanner head 230 but travels at half the speed. In this fashion, cables 236 and 237 remain taut throughout from one end 232 to the other end 234 even when scanner head 230 is in motion. In another embodiment, it is recognized that as the take-up mechanism operates over time, a certain amount of creep may develop in the cable. Thus, the take-up mechanism can be equipped with a spring or other tension device at one or both ends 232 and 234. This will prevent the cable from exhibiting excessive slack. Alternatively, the spring can be positioned in another part of the take-up mechanism such as between the pair of movable pulleys 221, 224. In this case, instead of being connected by a rigid member 228, a member with a spring device can be employed to connect the two of movable pulleys 221, 224.

As is apparent, in the cable take-up mechanism as shown in FIGS. 4A and 4B, the optical fiber cables are guided around a series of pulleys that determine the bend diameters of each optical fiber cable. The cables are maneuvered through a defined route. The set of translating pulleys 221, 224 allows the cables to stay under tension without the need of a spring or a loading device. The translating pulleys, which move in unison, assure that the tension on the cables is maintained essentially constant throughout each cable's length. Movement of the translating pulleys in a direction that is opposite to that of scanning head 230 serves to distribute each cable in the direction where it is needed in response to the forces that move the scanner head 230. As illustrated in FIGS. 4A and 4B, as the scanner head 230 moves from one side toward the middle of the cable take-up mechanism 210, reduction in the length of one cable between fixed turning pulley 214 and translating pulley 224 is offset or compensated by a corresponding increase in the length of the other cable between fixed turning pulley 218 and translating pulley 221.

Figure 5:
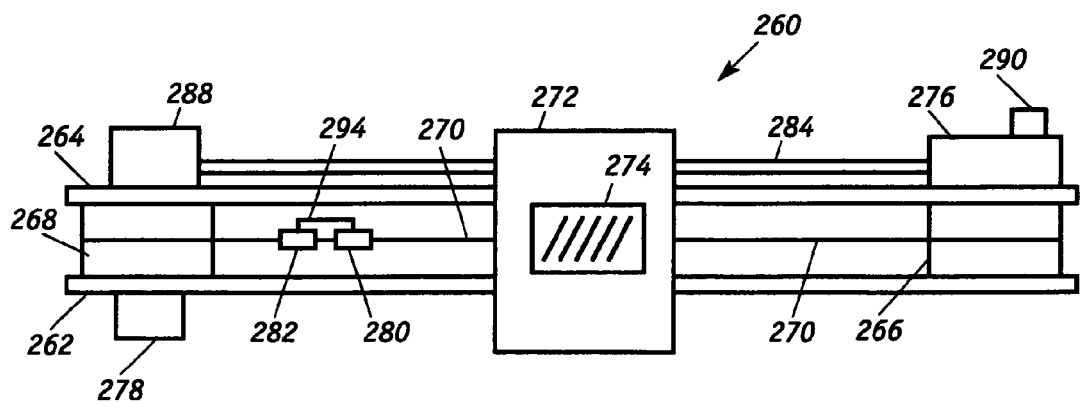
FIG. 5 is a top plan schematic view of a fiber optic cable take-up mechanism.

The scanner head 230 can be advanced back and forth along the cross direction by a number of mechanisms. In one embodiment, as illustrated in FIG. 5, the cable take-up mechanism 260 includes rails 262 and 264, fixed turning pulleys 266 and 268, and a pair of moving pulleys 280 and 282, which are linked by a rod 294. A carriage 272 rest on top of the rails 262, 264 which function as low-friction guides for the carriage 272 as it travels back and forth. The carriage 272, which can be a platform with rollers, supports scanner head 274. In this arrangement, the scanner head 274 is positioned underneath a web to be analyzed, however, it is understood that the cable take-up mechanism 260 can be employed so that the scanner head 274 is directly above or, at angle relative to, the web to measure properties from its top surface.

In the reflection mode, scanner head 274 houses the transmitter, detector and associated components while the pulsed laser source and spectrometric analyzer are in stationary compartment 278. Thus, detector signals are transmitted from scanner head 274 through cable 270 to compartment 278. Carriage 272 is connected to a belt 284 that is wound around drive pulley 276 and driven pulley 288 which is operatively connected to motor 290. In operation, control of motor 290 regulates the speed and direction of the movement of the carriage 272. Alternatively, belt 284 can be secured directly to the rod 294 which links the pair of movable pulleys 280, 282. In this fashion, activation of motor 290 also moves cable 270. As another alternative, motor 290 can be operatively connected to fixed turning pulley 266 to drive scanner head 274.

In the case where the scanning terahertz sensor is operating in the transmission mode as illustrated in FIG. 3A with separate take-up mechanisms on each side of the product being measured, cable take-mechanism 210 as illustrated in FIGS. 4A and 4B essentially operates the same way as described previously except that only one of cable 236 or 237 is a delivery fiber optic cable 6 or 16 (FIG. 3A). The other cable can comprise a non-active cable to maintain symmetry.

In the case where the scanning terahertz sensor is operating in the reflection mode as illustrated in FIG. 3B with a single take-up mechanism, cable take-mechanism 210 as illustrated in FIGS. 4A and 4B one of cable 236 or 237 consists of a single cable structure that includes both delivery fiber optic cables 6 and 16 (FIG. 3A). In this fashion, the two fiber optic cables are routed through the take-up mechanism along coextensive paths. The other cable can comprise a non-active cable to maintain symmetry. Alternatively, if the two delivery fiber optic cables are deployed separately but side-by-side, then the pulleys in take-up mechanism have dual grooves to accommodate them. The pair of non-active cables can be deployed side-by-side to maintain symmetry.

With the cable take-up mechanism, the total bend loss as the optical head moves back-and-forth during scanning is essentially preserved. This is important for scanners that use a spectroscopic sensor that measures the relative powers in two or more different wavelength bands. Bend loss in an optical fiber depends upon bend radius and total bend length. If the bend length or the bend radius changes as the mobile optical head is scanned, measurement errors will be introduced. The cable take-up mechanism keeps the angular bend length and the bend radius constant even as the optical head is moving; this in turn minimizes any sensor error. (Note however that the bend positions are changing.) The bend length for the optical fiber is analogous to the length of an arc, which is a segment of a circle. The bend length for an arc is equal to the product of the diameter and the angle between two radii as measured in degrees radian. Thus, an arc that spans 90 degrees has twice the bend length as an arc with the same radius that spans only 45 degrees. The cable take-up mechanism essentially maintains the same total bend length during scanning. Controlling the bend length and tension between the two delivery optical fiber cables 6 and 16 helps preserve the optical path difference between the power source and the detector optical fiber cables. This in turn minimizes or eliminates errors in temporal delay measurements which gauges the temporal delay in THz pulses that are caused by material properties of the sample, e.g., paper.

The scanning system can be employed to measure a variety of web or sheet properties such as fibrous sheets of paper in a papermaking machine, however, it is understood that the scanning system can be employed to measure properties of other materials, including, for example, plastics. In the art of making paper with modern high-speed machines, sheet properties must be continually monitored and controlled. The sheet variables that are most often measured include basis weight, moisture content, fiber orientation, temperature, and caliper, i.e., thickness, of the sheets at various stages in the manufacturing process. Papermaking devices are well known in the art and are described, for example, in U.S. Pat. No. 5,539,634 to Hu, U.S. Pat. No. 5,022,966 to Hu, U.S. Pat. No. 4,982,334 to Balakrishnan, U.S. Pat. No. 4,786,817 to Boissevain et al., and U.S. Pat. No. 4,767,935 to Anderson et al. which are incorporated herein by reference.

The foregoing has described the principles, preferred embodiments and modes of operation of the present invention. However, the invention should not be construed as being limited to the particular embodiments discussed. Thus, the above-described embodiments should be regarded as illustrative rather than restrictive, and it should be appreciated that variations may be made in those embodiments by workers skilled in the art without departing from the scope of the present invention as defined by the following claims.

What is claimed is:

1. A terahertz scanning sensor system for making temporal delay measurements of THz pulses that are caused upon interaction of such pulses with a moving sheet from which measurements material properties of the moving sheet can be detected, the system comprising:
   a mobile carriage reciprocally movable in a direction transverse to a direction of movement of the moving sheet;
   a THz transmitter and a THz detector each of which is carried by the mobile carriage and arranged such that THz radiation when emitted by the transmitter will interact with the sheet prior to such radiation being received at the detector;
   a laser source, an optical delay device and a beam splitter each of which is stationary with respect to the carriage, the laser source being operative to develop a laser pulse for application to the beam splitter, the beam splitter being operative to develop a first pulse and a second pulse in response to the laser pulse being applied thereto;
   a first optic fiber and a second optic fiber, each of the first optic fiber and the second optic fiber respectively having a first end and a second end, the first pulse being received at the first end of the first optic fiber for transmission along a first optical path to the second end thereof for illumination by the first pulse of the THz transmitter which in response thereto is operative to emit THz radiation, the second pulse being received at the first end of the second optic fiber for transmission along a second optical path to the second end thereof for illumination by the second pulse of the THz detector which in response thereto is operative to receive THz radiation, the first optic fiber and the second optic fiber being coextensively disposed so that the first optic fiber and the second optic fiber substantially maintain identical temperature gradients respectively along the first optical path and the second optical path; and
   a take-up mechanism in which a constant bend length and radius on each of the first optic fiber and the second optic fiber is maintained and further in which substantially the same tension on each of the first optic fiber and the second optic fiber is maintained as the mobile carriage is moved such that an optical path difference between the first optical path and the second optical path remains substantially constant whereby the first pulse and the second pulse transmitted respectively through the first optic fiber and the second optic fiber exhibit consistent (i) time of arrival, (ii) phase duration and (iii) polarization state and energy.

2. The scanning sensor system of claim 1 further comprising a modulated electrical input source operatively connected to the THz transmitter.

3. The scanning sensor system of claim 1 wherein the THz detector is operative to develop detection signals in response to radiation received, the system further comprising a spectrometric analyzer that processes the detection signals.

4. The scanning sensor system of claim 1 wherein the THz detector receives terahertz frequency radiation that is reflected or transmitted from the sheet.

5. A scanning sensor system as set forth in claim 1 wherein the take-up mechanism includes a pair of first pulleys stationary mounted and a pair of second pulleys carried by the mobile carriage, each of the pulleys having at least one groove in its outer perimeter into which the first optic fiber and the second optic fiber are threaded, the first end of each of the first optic fiber and the second optic fiber being fixed attached proximal to a selected one of the first pulleys and the second end of each of the first optic fiber and the second optic fiber being attached to the mobile carriage proximal to a selected one of the second pulleys.

6. A scanning sensor system as set forth in claim 5 wherein the first optic fiber and the second optic fiber are encased in a common cable structure.

7. A scanning sensor system as set forth in claim 5 wherein each of the pulleys has a double groove, the first optic fiber and the second optic fiber being adjacently disposed.

8. A scanning sensor system as set forth in claim 1 wherein the optical delay device is optically disposed intermediate the beam splitter and the first end of the second optic fiber and operative to induce delay in the second pulse thereby being operative to vary an effective length of the second optical path.

9. A scanning sensor system as set forth in claim 8 further comprising a first focusing lens optically disposed intermediate the beam splitter and the first end of the first optic fiber and a focusing lens optically disposed intermediate the optical delay device and the first end of the second optic fiber.

10. A scanning sensor system as set forth in claim 1 further comprising a first mirror optically disposed intermediate the THz transmitter and the sheet to direct radiation to the sheet and a second mirror optically disposed intermediate the sheet and the THz detector to direct radiation having interacted with the sheet to the THz detector.

* * * * *